(12) United States Patent
Joung Meyer et al.

(10) Patent No.: US 10,828,140 B2
(45) Date of Patent: *Nov. 10, 2020

(54) ARTIFICIAL URINARY SPHINCTER DEVICE

(71) Applicant: City of Hope, Duarte, CA (US)

(72) Inventors: Cassandra Rose Joung Meyer, Duarte, CA (US); Sophia Rose Williams, Duarte, CA (US); Jonathan Robert Wong, Duarte, CA (US); Meijing Maggie Liu, Duarte, CA (US); Risa Tom Egerter, Duarte, CA (US); Kevin Chan, Duarte, CA (US); Lori C. Bassman, Duarte, CA (US)

(73) Assignee: City of Hope, Duarte, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 16/159,280

(22) Filed: Oct. 12, 2018

(65) Prior Publication Data
US 2019/0110877 A1 Apr. 18, 2019

Related U.S. Application Data

(63) Continuation of application No. 15/076,973, filed on Mar. 22, 2016, now Pat. No. 10,098,720.

(60) Provisional application No. 62/136,828, filed on Mar. 23, 2015.

(51) Int. Cl.
*A61F 2/00* (2006.01)

(52) U.S. Cl.
CPC .................. *A61F 2/0036* (2013.01)

(58) Field of Classification Search
CPC ..... A61F 2/0004; A61F 2/0031; A61F 2/0036
USPC ..................................... 600/29–32
See application file for complete search history.

(56) References Cited

U.S. PATENT DOCUMENTS

| 6,689,046 | B2 | 2/2004 | Sayet et al. |
| 7,901,419 | B2 | 3/2011 | Bachmann et al. |
| 10,098,720 | B2* | 10/2018 | Joung Meyer ........ A61F 2/0036 |
| 2009/0247817 | A1 | 10/2009 | Forsell |

* cited by examiner

*Primary Examiner* — John P Lacyk
(74) *Attorney, Agent, or Firm* — Mintz Levin Cohn Ferris Glovsky and Popeo, P.C.

(57) ABSTRACT

An artificial urinary sphincter device is configured to be implanted in a relationship with a patient's urethra for the treatment of urinary incontinence. The size and shape of the device can vary for implantation on any of a wide variety of locations relative to the urethra such that it can exert a force onto the urethra for inhibiting or preventing involuntary leakage of urine.

24 Claims, 20 Drawing Sheets

ARTIFICIAL URINARY SPHINCTER DEVICE

REFERENCE TO PRIORITY DOCUMENT

This application is a continuation of U.S. patent application Ser. No. 15/076,973 filed on Mar. 22, 2016, issuing on Oct. 16, 2018 as patent Ser. No. 10/098,720 and entitled "Artificial Urinary Sphincter Device", and claims priority to U.S. Patent Application Ser. No. 62/136,828, filed on Mar. 23, 2015 and entitled "Artificial Urinary Sphincter Device", the contents of which are hereby incorporated by reference in their entirety.

BACKGROUND

Urinary incontinence (UI) is a loss of bladder control that results in occasional or regular leakage of urine out of the bladder in an individual. It can be a common and distressing condition in that urinary leakage can occur upon normal movement or action of the person, such as when the person coughs or sneezes.

The treatment of urinary incontinence can vary. One type of treatment involves the implantation of an artificial urinary sphincter on to a person's urethra. There are a variety of disadvantages associated with the current artificial urinary sphincter. For example, such sphincters are surgically implanted and such surgery can take a great amount of time due to the high number of incisions required during implantation. Moreover, existing implants can be formed of several separate pieces that must be connected together by the surgeon using devices such as clamps, which can be tedious and unwieldy. In addition to being a tedious implantation process, the connected pieces can form points of failure for the device after implantation.

In addition, because the device is implanted in tissue, there is a tendency for the device to damage or irritate tissue in which it is planted. The device can also be difficult for patients to actuate, as the device can be hard to isolate and squeeze. The target audience of such devices are often older patients who can be lacking in dexterity, which can make it even more difficult for such patients to actuate the device.

In view of the foregoing, there is a need for improved devices for treating urinary incontinence.

SUMMARY

An artificial urinary sphincter device is configured to be implanted in a relationship with a patient's urethra for the treatment of urinary incontinence. The size and shape of the device can vary for implantation on any of a wide variety of locations relative to the urethra such that it can exert a force onto the urethra for inhibiting or preventing involuntary leakage of urine.

In one aspect, there is disclosed an artificial urinary sphincter for treating urinary incontinence, comprising: a body defining a urethral opening sized and shaped to receive a urethra upon the body being implanted into a patient; at least one force member movably attached to the body, the force member configured to move between a closed position wherein the force member exerts a force onto the urethra sufficient to inhibit urine flow through the urethra when implanted, and an open position wherein the force member does not inhibit fluid flow through the urethra when implanted; and an actuation assembly coupled to the body, the actuation assembly including an actuator coupled to an actuation mechanism, wherein the actuation mechanism couples the actuator to the at least one force member so that actuation mechanism causes movement of the force member between the closed position and the open position upon actuation of the actuator.

Other features and advantages should be apparent from the following description of various implementations, which illustrate, by way of example, the principles of the disclosure.

DETAILED DESCRIPTION

An artificial urinary sphincter device is configured to be implanted in a relationship with a patient's urethra for the treatment of urinary incontinence. The size and shape of the device can vary for implantation on any of a wide variety of locations relative to the urethra such that it can exert a force onto the urethra for inhibiting or preventing involuntary leakage of urine.

In an embodiment, the device is sized and shaped to be implanted on an inferior side of the bulbar urethra in a male subject. In another embodiment, the device is sized and shaped to be implanted on a superior side of the urethra in a female subject. The device is configured to transition between at least two states including (1) a first, closed state in which the device inhibits or prevents involuntary leakage of urine through the urethra by exerting a force on the urethra in a manner sufficient to inhibit or prevent urine flow through the urethra; and (2) a second, open state in which the device does not inhibit or prevent involuntary leakage of urine through the urethra. Either the open state or the closed state may be a default state of the device. A user can transition the device between the closed state and the open state by operating an actuator, such as a button, coupled to the device, as described in more detail below. The button may be located on the device or may be remotely located relative to the device.

Figure 1:
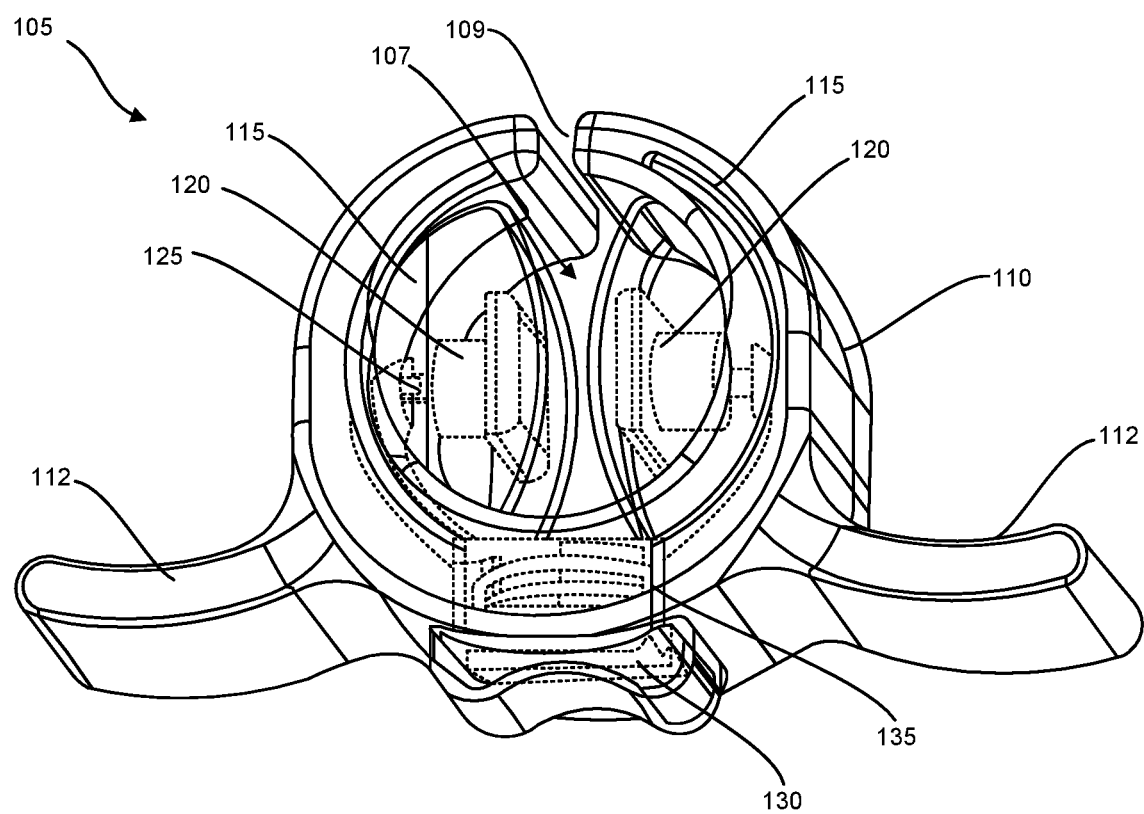
FIG. 1 shows a perspective view of an artificial urinary sphincter device.

FIG. 1 shows a perspective view of an artificial urinary sphincter device 105, which is formed of an annular or partially annular body or cuff that may have any of a variety of sizes to fit various urethra diameters. The device 105 defines a circular or substantially central urethral opening 107 sized to receive a urethra such that the device 105 can form a ring around the urethra when implanted in a patient. In this regard, the device 105 includes a gap 109 that provides a passageway through which the urethra can be inserted into the urethral opening during implantation. The gap 109 provides the device 105 with a C-shape.

The device 105 is formed of an atraumatic, outer membrane or casing 110 that at least partially contains an internal, rigid skeleton 115 embedded in the casing 110. The casing 110 can be made of a relatively soft material and can have a rounded, atraumatic shape that does not irritate or damage adjacent tissue when implanted on the urethra. The casing 110 can include one or more retaining members, such as wings 112 that are sized and shaped to interact with tissue to keep the device in a fixed position relative to tissue once implanted.

The device 105 further includes one or more movable force members 120 that are sized, shaped, and positioned to apply pressure to the urethra when the device is implanted for inhibiting or preventing involuntary leakage of urine through the urethra, as described in more detail below. In an embodiment, the force members are configured to compress at least a portion of the urethra. The device 105 further includes at least one coupling member such as actuation wires 125 that directly or indirectly connects the force members 120 to an actuation assembly for actuating the force members 120. In an example embodiment, the actuation assembly includes an actuator, such as a button 130, coupled to an actuation mechanism 135 that transitions the force members between open and closed states upon a user actuating the button 130.

With reference still to FIG. 1, the casing 110 and the skeleton 115 provide the general, overall shape of the device's outer periphery. The casing 110 forms the rounded, outer periphery of the device 105. The two force members 120 are positioned in an opposed relationship such that they face one another and extend into or toward the urethral opening 107 in a manner that permits them to apply a force to the urethra when implanted. The button 130 is positioned along an inferior region of the casing between the wings 112, which extend outwardly from the outer periphery of the casing 110. The button 130 is sufficiently large for a patient to locate it and palpate it through the perineum when the device is implanted. In order to avoid accidental presses of the button, an outermost surface of the button (or membrane covering the button) can be flush with an outer surface of the casing 110.

In another embodiment, the actuation assembly including the button 130 and actuation mechanism 135 is at least partially positioned in a remote location from the casing 110 and skeleton 115.

Figure 2:
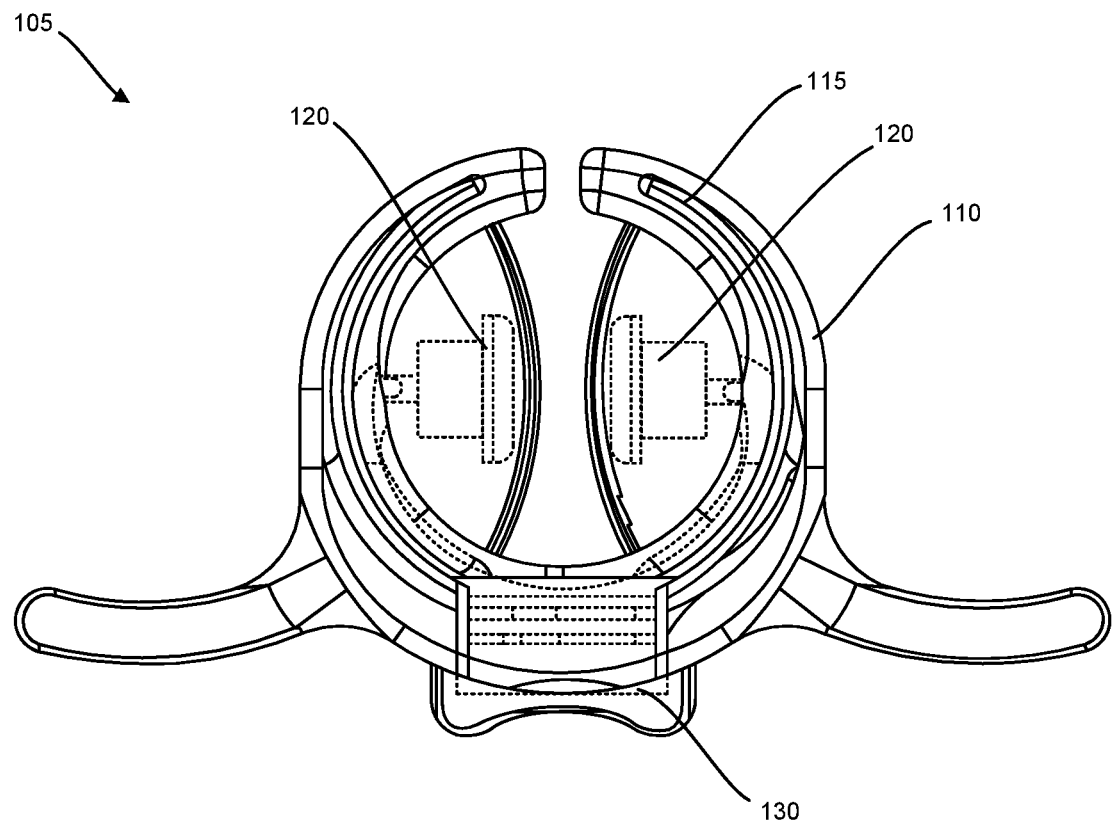
FIG. 2 shows a side view of the device.
Figure 3:
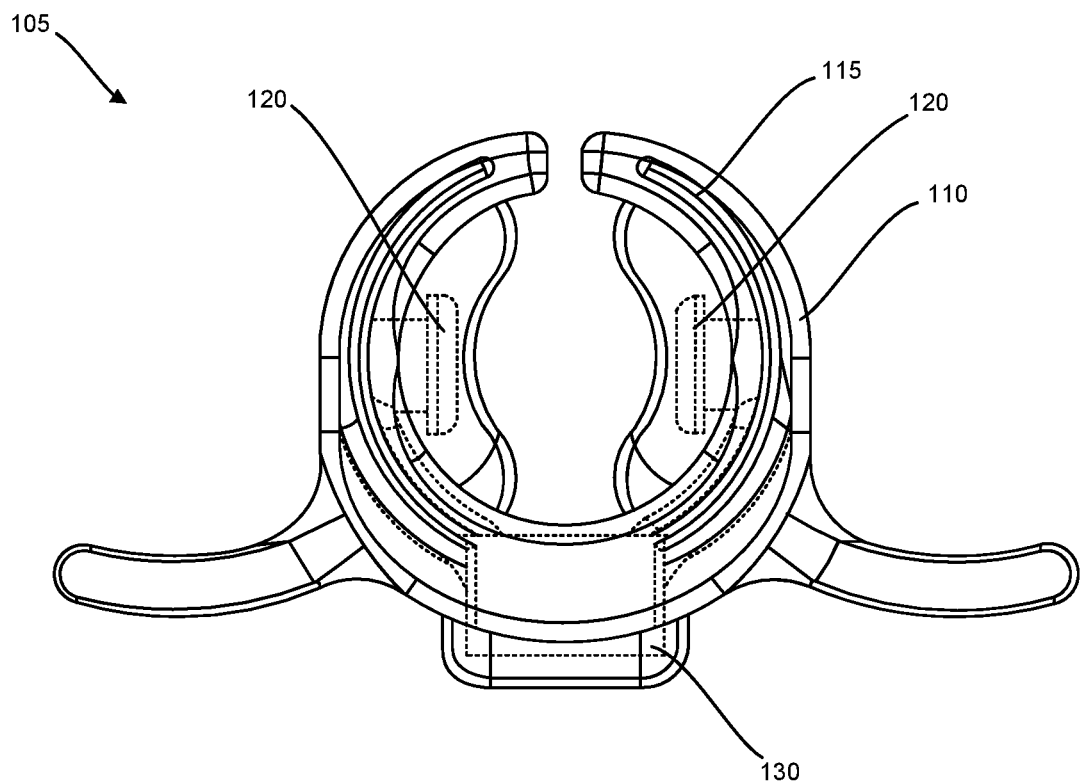
FIG. 3 shows a side view of the device in the open state.

FIG. 2 shows a side view of the device 105 in the closed state wherein the force members 120 are separated by a distance such that the force members 120 collectively or individually apply pressure to the urethra when the device is implanted. That is, at least a portion of the urethra is positioned between the force members 120 in the implanted device such that they can individually or collectively apply pressure to the urethra. FIG. 3 shows a side view of the device 105 in the open state wherein the force members 120 are further separated from one another (relative to the closed state) such that the force members 120 do not apply pressure to the urethra when implanted. A user can actuate the button 130 (such as by pressing on the button 130) to transition the force members 120 between the closed state and the open state. In a non-limiting example, a male user actuates the button 130 by pressing on the button 130 through the perineum. In another non-limiting example, in a female user, the button is remotely located in an anterior pelvic region or other anatomically convenient location.

The wires 125 are at least partially disposed in the skeleton 115, as described in more detail below with reference to FIGS. 6-10. The wires 125 connect the button 130 to the force members 120 in a manner that causes the force members to move between the open state and the closed state when the button 130 is actuated. For example, when the button is pushed, the wires are forced through wire tracks guide members 615 (FIG. 6) in the skeleton 115 in a manner that displaces the force members 120 between the open state and close state. In an embodiment, actuation of the button 130 transitions the force members 120 between two discrete positions: the open position (shown in FIG. 3) and the closed position (shown in FIG. 2). In this regard, the wires 125 can be considered part of the actuation assembly although they are not necessarily part of the actuation assembly.

The various components of the device 105 are now described in detail. It should be appreciated that the structure and assembly of the device 105 can vary from the examples described herein and that the device is not limited to the components described herein.

Casing

As mentioned, the outer periphery of the device is formed by an outer casing 110 that contains the internal skeleton 115. The casing 110 is formed of a relatively soft material that overlies the more rigid skeleton 115, which is sufficiently rigid to provide and maintain the general shape of the device 105.

Figure 4A:
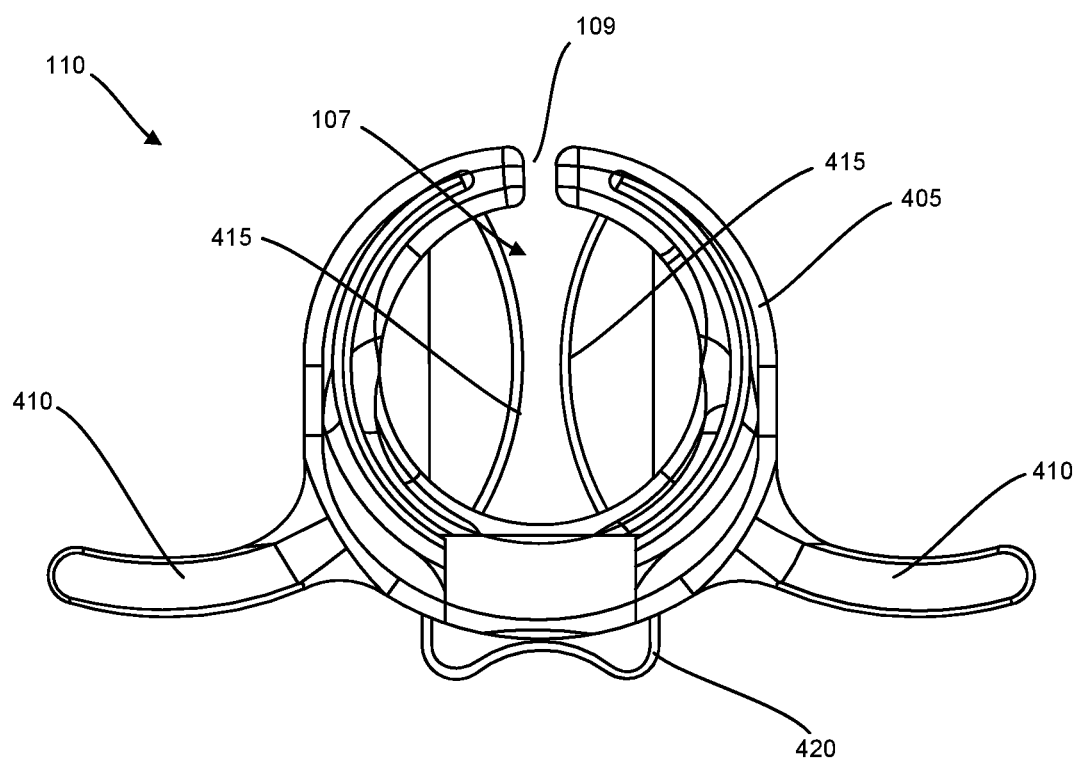
FIG. 4A shows a side view of a casing of the device.
Figure 4B:
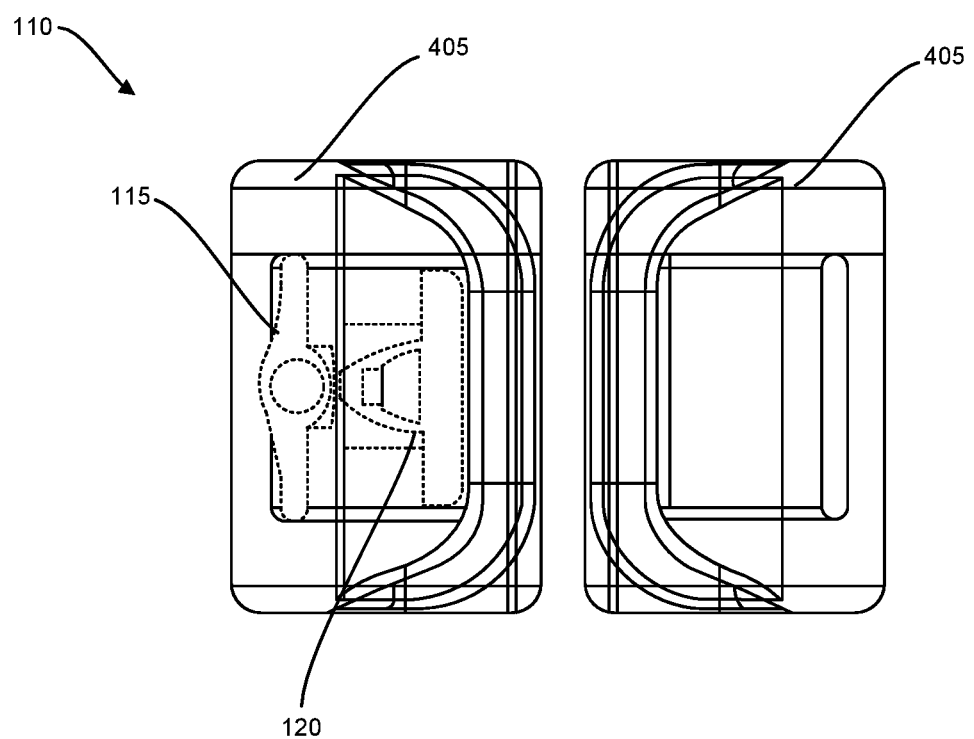
FIG. 4B shows a cross sectional view of a casing of the device.

FIG. 4A shows a side view of the casing 110, which is formed of a C-shaped main body 405 and a pair of wings shaped regions 410 that define the device's wings. The casing 110 is sized and shaped to encompass the skeleton 115 and to provide a soft, smooth, medical grade barrier between any rigid pieces (such as the skeleton 115 and the button number 130) of the device 110 and surrounding tissue when the device 110 is implanted in contact with the urethra. The casing 110 can vary in thickness. In an embodiment, the thickness of the casing varies at different locations relative to where the casing 110 is located on the skeleton. For example, as shown in the cross-sectional view of FIG. 4B, the thickness of the casing can vary due to the topography of the skeleton 115 and the circumference of the casing 110. The casing 110 can taper to a thinner thickness and cross-section in order to accommodate surrounding tissues and membranes.

A pair of membranes 415 is attached to the casing 110 and positioned inside the urethral opening 107 such that the membranes 415 cover the force members 120 in the assembled device 105. Another membrane 420 is located at the position of the button 130, such as on the inferior surface of the device 105, and is configured to cover the button 130 in the assembled device.

The membranes are attached to the casing in a sealed relationship such that they cover the force members and the button in a manner sufficient to prevent bodily fluids from entering the device at these locations. The membranes also provide an atraumatic/soft surface over the force members and the button so as to prevent tissue from being pinched by movement of the mechanisms of the device. The membranes are thin and flexible and are passive in that they do not affect or alter movement of the compression pieces or the button. The membranes can be manufactured in an unsealed relationship with the casing 110 in order to permit the compression members and the button to be attached to the device. The membranes can then be sealed to the casing 110 during manufacture to provide a fluid tight seal.

Figure 5A:
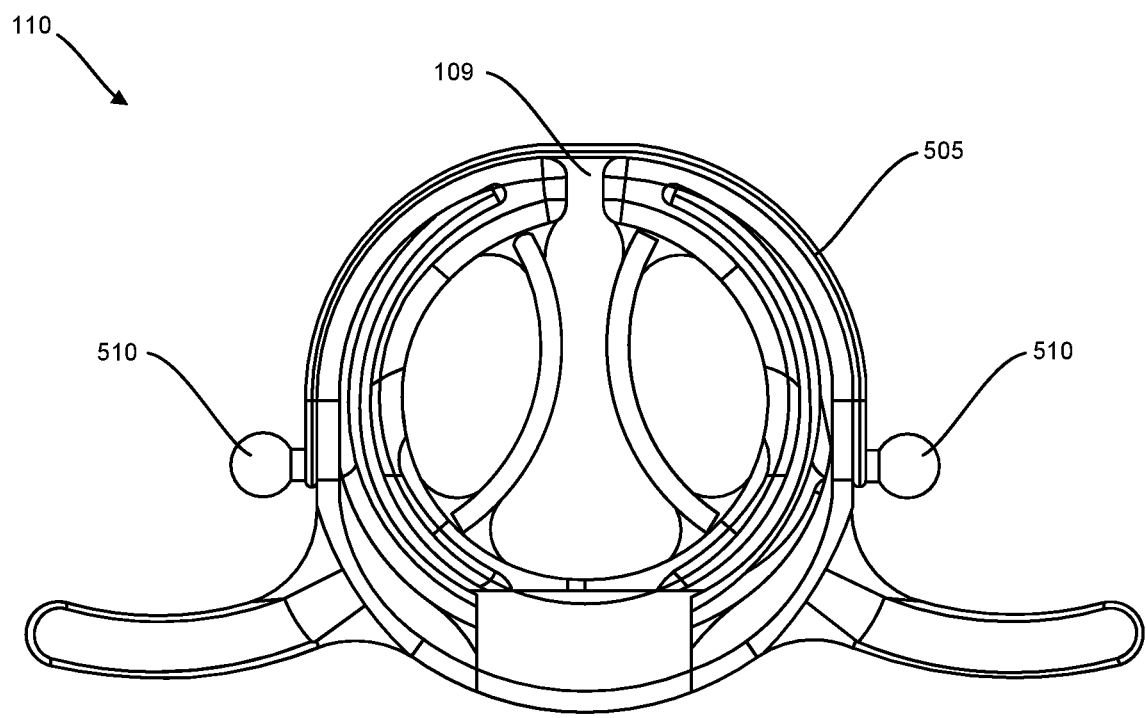
FIGS. 5A and 5B show the device with a strap member.
Figure 5B:
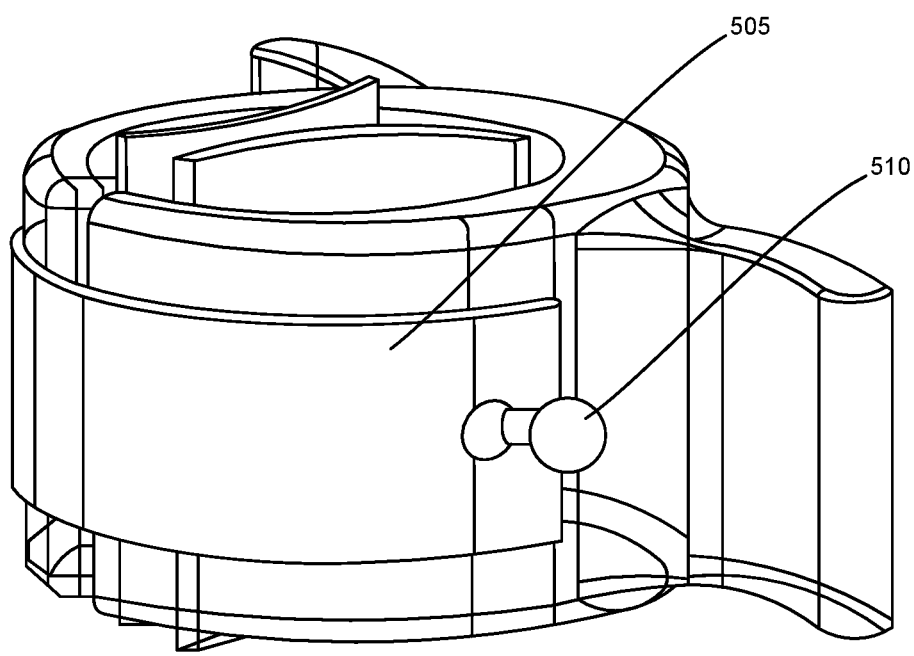

As mentioned, the casing 110 forms a gap 109 that provides a passageway for the urethra to be inserted into the urethral opening 107 during an implantation procedure. In order to bolster or secure the device's placement or position around the urethra, a strap 505 can be positioned on the device 105 such that the strap 505 covers the gap 109, as shown in FIGS. 5A and 5B. The strap 505 can extend from one side of the outer surface of the casing to an opposite side of the outer surface of the casing such that it covers the gap 109 and wraps about the superior surface of the bulbar urethra. In order to position the strap, a surgeon may be required to cut through the tunica albuginea during implantation of the device.

The strap 505 can be attached to the device 110 in any of a variety of manners. For example, the strap 505 may be molded to the casing 110 on one end and attached on its opposite into the casing using an attachment mechanism, such as a knob that inserts through a hole in the casing and/or the strap 505. In another example, a knob is pre-positioned on one or more locations on the casing 110 such that a detached strap 505 can then be attached to the device 110 by the surgeon by securing the strap 505 to the knobs such as on opposite ends of the strap 505.

With reference again to FIG. 4A, the wings 112 are extensions, such as curved extensions, that protrude laterally from the outer periphery of the casing 110 at locations near the button 130. In an embodiment, the wings 112 are sized and shaped to cup or otherwise engage the corporal bodies behind the urethra to help prevent the casing 110 from displacing along or around the urethra during actuation of the device or during normal movement of the patient. The wings 112 are made of a flexible material, such as medical grade silicone. The wings 112 can be manufactured as an integral or monolithic portion of the casing 110. A connection location between the casing 110 in the wings 112 can be filleted to provide a strengthened connection.

Skeleton

Figure 6:
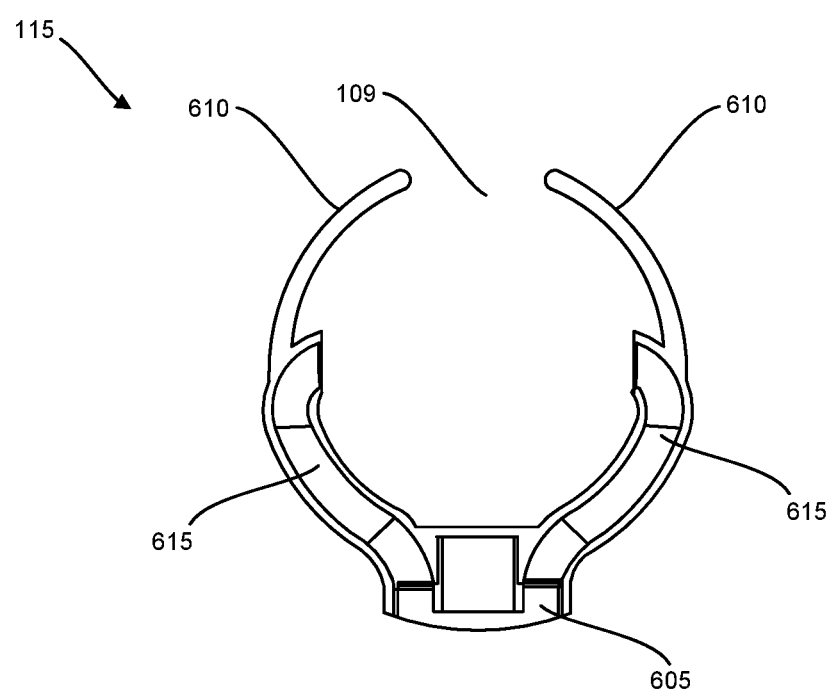
FIG. 6 shows a side view of an example skeleton of the device.
Figure 7:
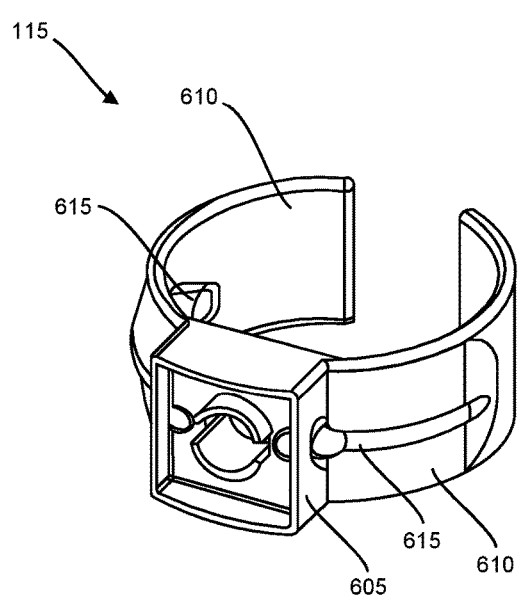
FIG. 7 and FIG. 8 show perspective views of the skeleton.
Figure 8:
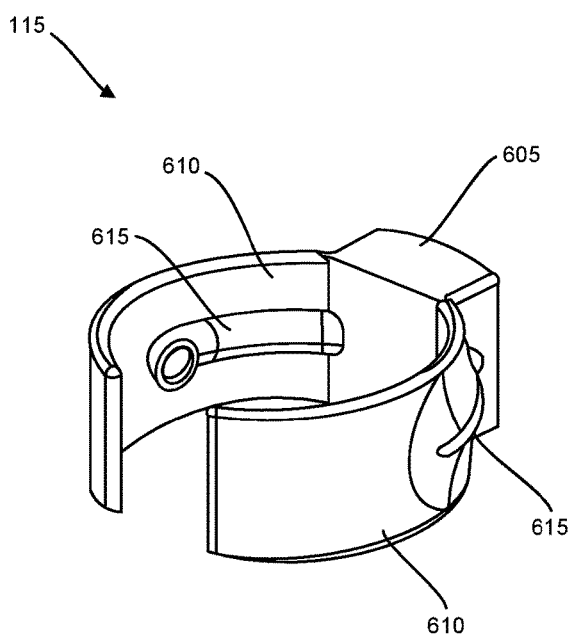
Figure 9:
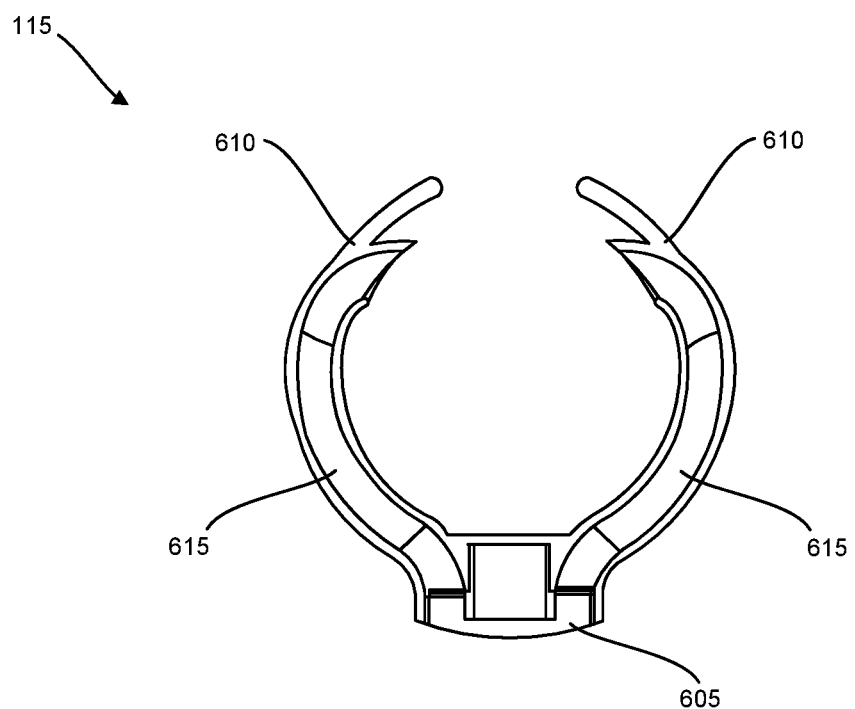
FIG. 9 shows a side view of an example skeleton of the device.

FIG. 6 shows a side view of an example skeleton 115 of the device 105. FIG. 7 and FIG. 8 show perspective views of the skeleton 115. The skeleton 115 is a generally annular or partially annular structure that forms a C-shape. As mentioned, the skeleton 115 is embedded within the casing 110 in the assembled device. The skeleton 115 is at least partially made of a material that is more rigid than the material of the casing 110 so that the skeleton 115 provides a structurally supportive framework for the device 105. As mentioned, the outer casing is softer to provide an atraumatic contact surface for the urethra and surrounding tissues. The rigid skeleton 115 maintains the shape of the device 105 and its rigidity assists in keeping it in a fixed position around the bulbar urethra. Although the skeleton 115 is rigid, it also has some flexibility to permit the device 105 to be manipulated onto the urethra during implantation. The flexibility of the skeleton 115 can be achieved via material properties and/or mechanical properties, such as a hinge mechanism on the skeleton 115.

With reference to FIG. 6-8, the skeleton 115 is formed a base member 605 that is positioned on an inferior region of the device. The base member 605 provides a protective housing for the button 130 and at least a portion of the actuation assembly. The base member 605 defines a space or cavity adequately sized to contain the button 130 and actuation mechanism and also for attachment of the actuation wires 125 to the button 130 as well as any other parts of the actuation assembly.

A pair of curved ribs or extensions 610 extend outwardly from the base member 605. In the example embodiment shown in FIGS. 6-8, the extensions 610 are thin, curved strips of material that collectively define a generally cylindrical shape or C-shape with the gap 109 positioned opposite the base member 605. The extensions 610 provide structural support for the overall shape of the device 110. In this regard, the extensions 610 can have a variety of shapes and sizes adapted to provide proper structural support so that the device can be positioned around the urethra. In an embodiment, the extensions 610 are made of a solid material. In another embodiment, the extensions 610 are made of mesh material. It should be appreciated that other materials can be used to form the extensions or any part of the skeleton.

A pair of guide members 615 are disposed along the extensions 610 so as to provide a guide pathway for the actuation wires 125 to run from the button 130 to the force members 120 in the assembled device. In the example embodiment, the guide members 615 are tubular structures each having a first end located at the base member 605 and a second end positioned along an extension 610. Each guide member 615 defines an internal lumen with a first opening at the base member 605 and a second opening at a location where a respective force member 120 is located. In this manner, the guide members 615 provide a pathway for the actuation wires to run from the button number 130 to the force members 120. The guide members 615 provide a protective covering for the actuation wires and also provide a shield that prevents material wear between the actuation wires and the casing 110. The dimensions of the internal lumens of the guide members 615 can vary based on the dimensions of the actuation wires. In an embodiment the internal lumens are only slightly larger in diameter than the diameter of the wires.

The length of the guide members 615 can vary based upon the location of the force members 120 and/or an angle at which the force members 120 extend into the opening 107. For example, FIGS. 6-8 show an embodiment wherein the guide members 615 to from the base 605 to about midway of the device. In another example embodiment shown in FIG. 9, the guide members 615 are longer than the embodiment shown in FIGS. 6-8. It should be appreciated that the guide members 615 can have any of a variety of lengths selected to position the force members at desired locations and/or orientations.

The actuation wires 125 that run through the guide members may vary in material and in structural configuration. In an example embodiment, the wires are braided wires or spring members. The wires can be made of a material that can achieve actuation between the button and the force members without kinking.

Figure 10:
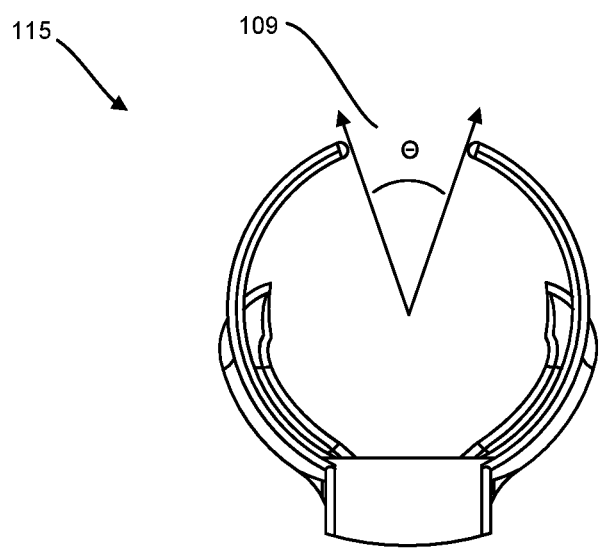
FIG. 10 shows a side view of an example skeleton of the device.

As discussed, a gap 109 is located along the periphery of the device 105, such as at a superior region of the device. With reference to FIG. 10, the skeleton 115 includes this gap 109. The size of the gap 109 can vary and can be larger in the skeleton 115 than in the assembled device 105 due to the presence of the casing 110 that overlies the skeleton 115. The gap in the skeleton 115 can vary in size and can be defined by an angle $\theta$ between a center of the device and the ends of the extensions 610. The value of the angle $\theta$ may vary and may be selected to provide a desired opening size to accommodate the tunica albuginea when the device is implanted. In an embodiment, the angle is less than 90 degrees. The angle may be large enough to accommodate the urethra during surgery and to accommodate the tunica albuginea while implanted, but small enough to discourage movement of the device against the urethra.

Force Members

As discussed, the force members 120 are configured to provide a force, such as a compressive force, to the urethra. As shown in FIG. 1, the force members 120 are positioned facing one another in an opposed relationship and extending into the urethral opening 107 such that they can interface with and provide a force to the urethra when the urethra is positioned in the urethral opening 107.

The force members 120 can extend into the opening 107 at any of a variety of angles relative to one another and/or relative to the center of the device. A magnitude and an orientation of force vector provided by each force member can be selected to provide a desired compression to the urethra. The force members may press laterally from opposite sides on to the urethra such that the force vectors provided by the force members are parallel and/or coaxial. Alternately, the force vectors can be nonparallel to one another.

In an embodiment, the actuation assembly maintains the force members in either the closed state (wherein they compress the urethra to prevent or restrict urine flow) or the open state (wherein they are positioned to allow urine flow) based on a position of the button 130. Alternately, the force members 120 can be biased toward one of the open state or the closed state so that the force members are in one of the states as a default. When in the open state, the force members are slightly positioned or inserted into the casing 110 such that they do not extend into the opening 107 or extend only slightly into the opening 107 to permit maximum expansion room for the uncompressed urethra.

Figure 11A:
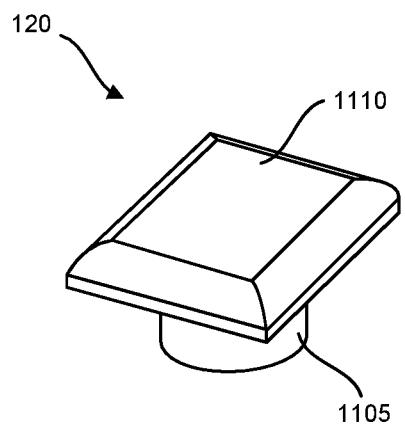
FIGS. 11A and 11B show perspective and side views of an example force member of the device.
Figure 11B:
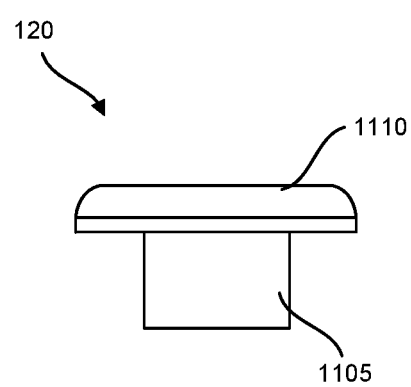
Figure 12A:
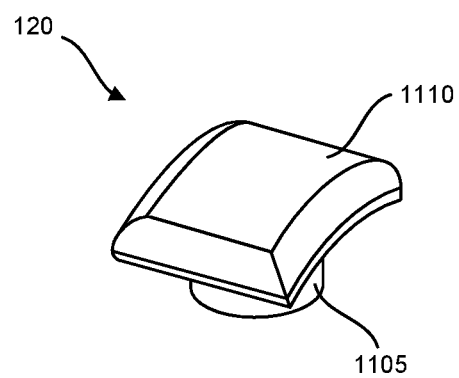
FIGS. 12A and 12B show perspective and side views of an example force member of the device.
Figure 12B:
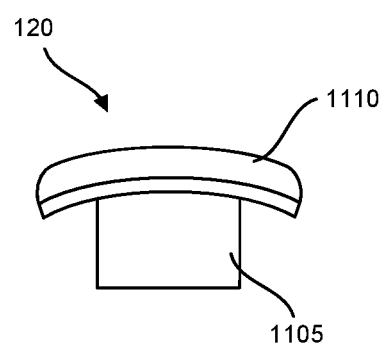
Figure 13A:
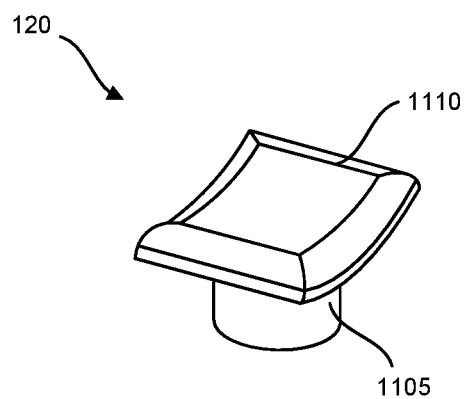
FIGS. 13A and 13B show perspective and side views of an example force member of the device.
Figure 13B:
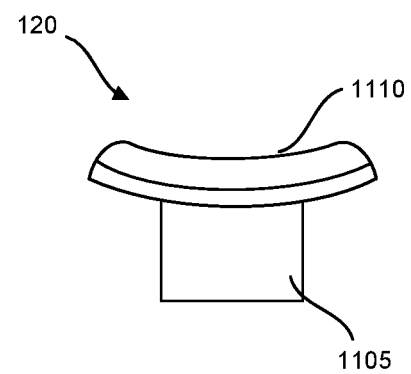

The force members 120 can vary in structure. FIGS. 11A and 11B show perspective and side views, respectively, of an example force member 120, which has a base 1105 that supports a platform 1110 having an abutment surface that faces and/or contacts the urethra when implanted. In the embodiment of FIG. 11A. The base 1105 is rounded or circular and the platform 1110 is rectangular with a substantially flat abutment surface with chamfered edges. It should be appreciated that the size, shape, and contour of the base 1105, platform 1110, and abutment surface can vary to provide a desired amount and type of force to the urethra. For example, FIGS. 12A and 12B show another embodiment wherein the platform 1110 is shaped to provide a convex abutment surface. In another example embodiment shown in FIGS. 13A and 13B, the platform 1110 is shaped to provide a concave abutment surface.

The force members 120 are at least partially made of a material that is sufficiently rigid so that they can apply a force to the urethra without deforming. In an embodiment the force members are made of a rigid plastic. The force members 120 can include a softer outer layer of material, such as silicone, that reduces or eliminates the likelihood of the force members damaging the membrane 445 (FIG. 4A) or the urethra. As mentioned, the force members 120 are mechanically connected to the button 130 via the actuation wires, which run through the guide members 615 (FIG. 6).

Actuation Assembly

Figure 14:
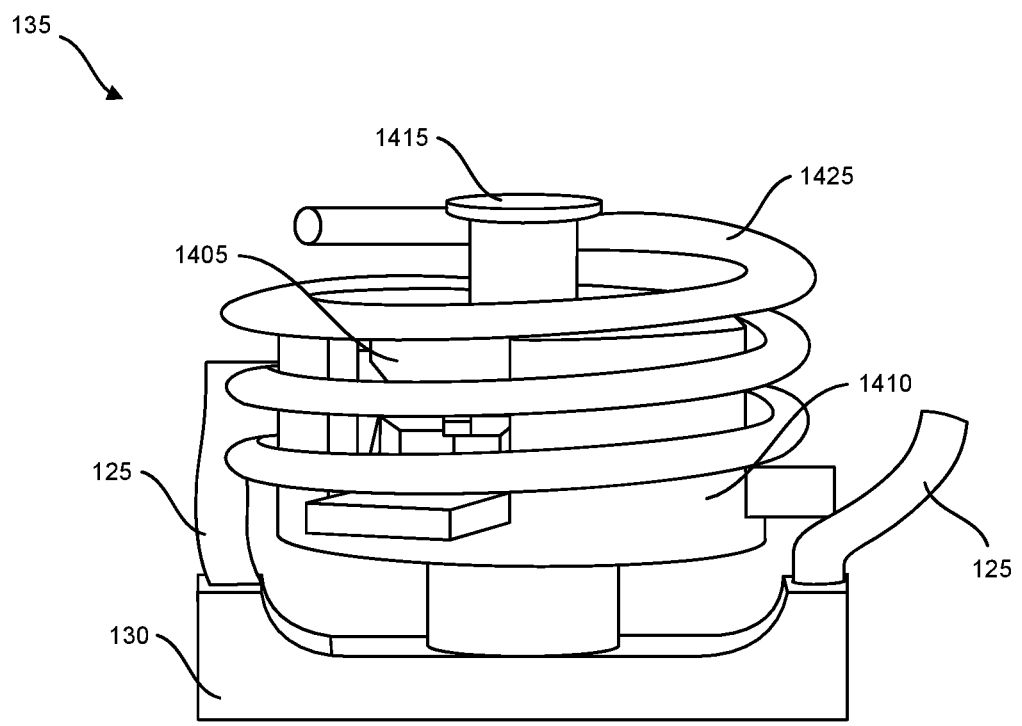
FIG. 14 shows an actuation assembly of the device in an assembled state.
Figure 15:
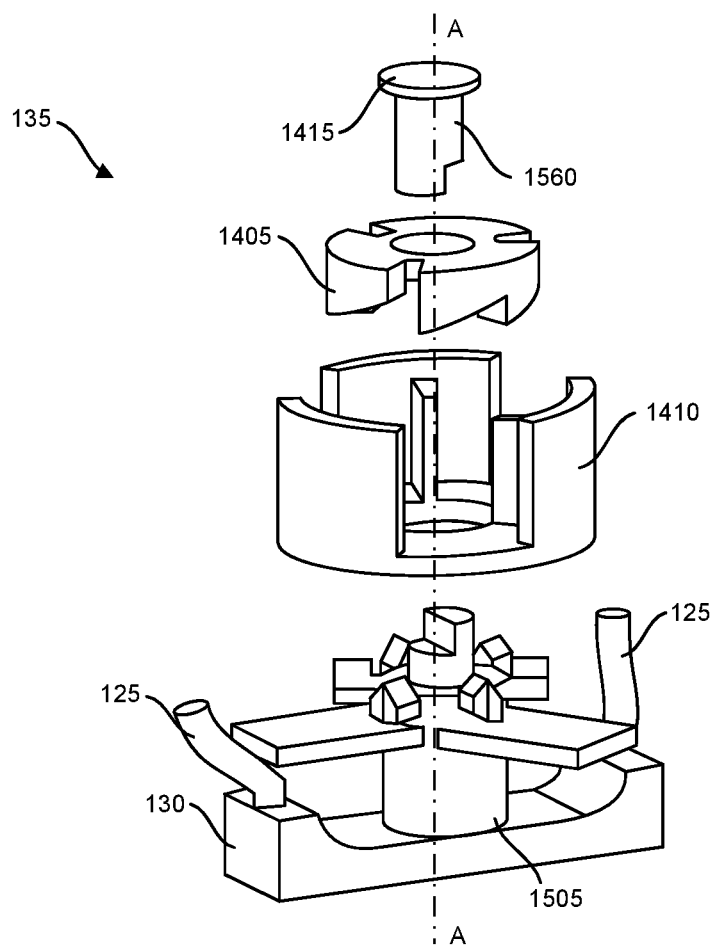
FIG. 15 shows an exploded view of the actuation assembly.

The actuation assembly includes the button 130 and actuation mechanism 135. The actuation assembly is actuated to transition the device 105 between the open state and the closed state. As mentioned, the actuation assembly is maintained between two discrete states—the open state and the closed state—based on the position of the button number 130. FIG. 14 shows the actuation assembly in an assembled state. FIG. 15 shows an exploded view of the actuation assembly. The assembled actuation assembly is sized and shaped to fit at least partially within the base member 605 (FIG. 6) of the skeleton 610. When positioned within the base member 605 of the skeleton 610 of the assembled device, the button 130 is oriented and positioned so that a user can exert a force onto the button, such as with his or her finger, to actuate the actuation assembly.

The actuation assembly includes the button 130, a cam member 1405, a guide piece 1410, a peg 1415, and a biasing member such as a spring 1425. The components of the actuation assembly interlock and/or mate with one another and move relative to one another in a relationship that transmits motion of the button to motion of the force members 120 via the actuation wires, which are attached at one end to the button 130 and at an opposite end to the force members 120.

Figure 16:
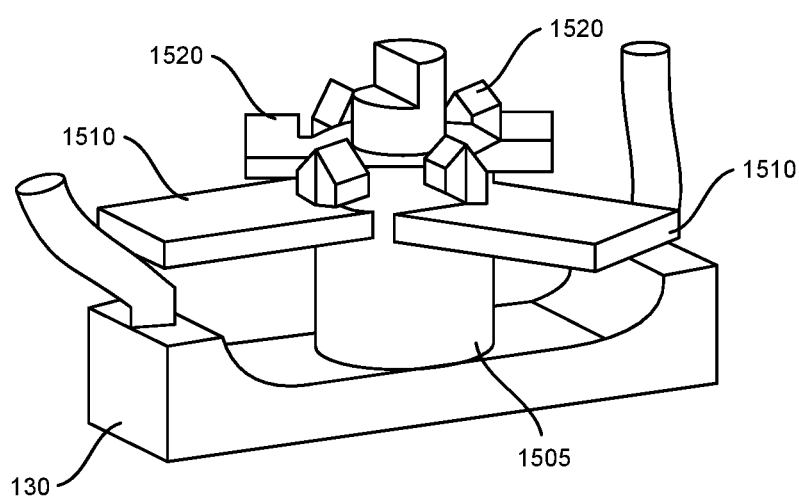
FIG. 16 shows an enlarged view of a button of the actuation assembly.

As shown in FIG. 15, a column 1505 extends outwardly from the button 130 along an axis A. The guide piece 1410, the cam member 1405, and the peg 1415 coaxially aligned with the axis A. FIG. 16 shows an enlarged view of the button 130. A plurality of cantilevered beams 1510 radiate outward from the column 1505. In addition, a plurality of structures 1520 at an upper region of the column 1505 form several upwardly facing, inclined surfaces. An uppermost end of the column 1505 defines a pair of stepped surfaces including a lower surface in an upper surface.

Figure 17:
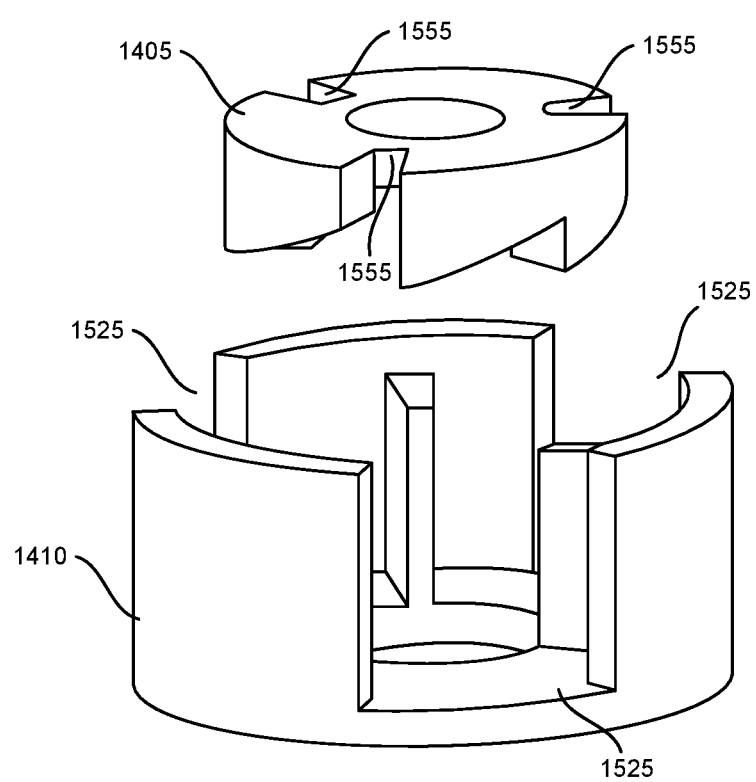
FIG. 17 shows an enlarged view of a guide piece and a cam member of the actuation assembly.

FIG. 17 shows an enlarged view of the guide piece 1410 and the cam member 1405. The guide piece 1410 has a substantially cylindrical shape with spaced apart cutouts or windows 1525 that are positioned to align with and receive the cantilevered beams 1510 (FIG. 16) of the button 130. The guide piece 1410 has a bottom opening through which the column 1505 of the button 130 extends in the assembled actuation assembly with the cantilevered beams 1510 extending outwardly through the windows 1525 of the guide piece 1410, as shown in FIG. 14.

As shown in the enlarged view of FIG. 17, the cam member 1405 also has a substantially cylindrical shape sized to fit within the guide piece 1410. A center opening of the cam member 1405 is coaxial with the axis A (FIG. 15) and is sized to receive the column 1505 of the button 130. The cam member 1405 has a plurality of slots 1555 that align with and receive corresponding ribs on internal surfaces of the guide piece 1410. In addition, the cam member 1405 forms a plurality of downwardly facing, inclined surfaces that slidingly engage the upwardly facing, inclined surfaces of the column 1505 of the button 130.

With reference again to FIG. 15, the peg 1415 has a column 1560 that is coaxially aligned with the axis A. A bottom surface of the peg 1415 defines a pair of downwardly facing stepped surfaces that engage complementary stepped surfaces of the column 1505 of the button 130. As mentioned, and as shown in FIG. 14, the button 130, cam member 1405, guide piece number 1410, and peg 1415 nest together and coaxially aligned along the axis A in the assembled actuation assembly. When nested as such, the spring 1425 positions over and surrounds the outer surface of the guide piece 1410 with a bottom surface of the spring 1425 being supported by the cantilevered beams 1510. In the assembled device, actuation assembly fits in and is housed within the base 605 (FIG. 6) of the skeleton with an actuation surface of the button 130 facing outward for access by a patient.

Figure 18:
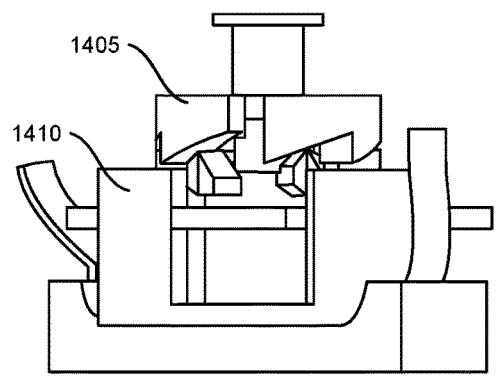
FIGS. 18 and 19 show an actuation process of the actuation assembly.
Figure 19:
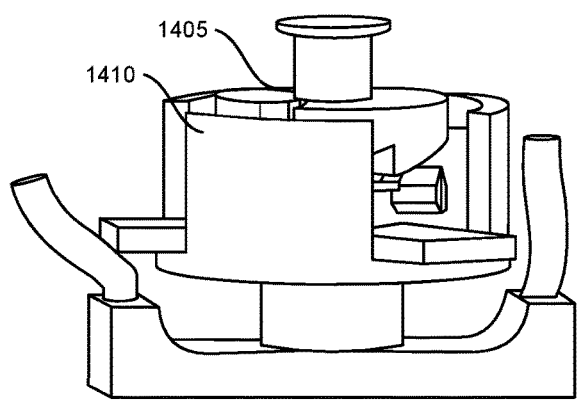

The actuation assembly operates as follows. As mentioned, the push button mechanism maintains the two discrete states of the device 105—open and closed. The guide piece 1410 enforces the linear motion of the other parts of the actuation assembly by virtue of the cantilevered beams 1510 extending outwardly through the straight windows 1525 of the guide piece 1410. The rotating cam member 1405 locks into two different positions along the guide piece 1410: either inside the guide piece 1410 (as shown in FIG. 18) or extended out past an upper edge of the guide piece 1410 (as shown in FIG. 19). The button column 1505 drives the rotating cam 1405 into the two different positions by virtue of the sliding engagement between the upwardly facing inclined surfaces on the button column 1505 and the downwardly facing inclined surfaces on the rotating cam 1405.

The spring 1525, which surrounds the guide piece 1410 (as shown in FIG. 14), maintains an upward force so that the two different states are held in place. The spring 1525 is strong enough to pull the actuation wires 125 connected to the force members. The peg 1415 extends through the rotating cam 1405 to keep the rotating cam 1405 and the button 130 at the same relative distance at all times, allowing the actuation wires attached to the button to follow the two positions of the rotating cam 1405 and thereby move the force members 120 between the open and closed states.

It should be appreciated that the actuation assembly can vary in structure and mechanical configuration and is not limited to the example embodiment shown herein.

Assembly of the Device

The device 105 can be provided as a single component, assembled system to the surgeon. As discussed, the device is formed of several pieces, which are manufactured separately and assembled into the final device. Some non-limiting examples of how the device 105 is assembled are now described.

Figure 20:
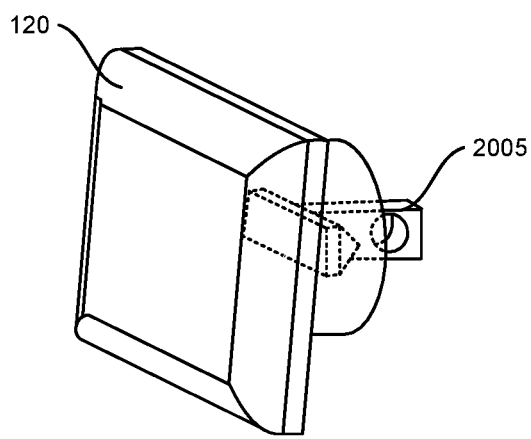
FIG. 20 shows a portion of the actuation assembly.

The actuation wire 125 and the force members 120 are connected in an example embodiment by a lock and pull system. A first tip of the actuation wire has a rigid attachment piece 2005 (such as plastic) shaped to mate with a corresponding piece on the force member 120. In an example, the attachment piece 2005 is T-shaped, as shown in FIG. 20. A tip of the attachment piece 2005 is connected to the actuation wire (not shown in FIG. 20), such as by a small peg at the bottom of the T shape. The tip of the actuation wire is inserted into a slot at the end of the attachment piece 2005 and then manipulated to be pulled/fitted into a second slot. This connects the force member 120 and the actuation wire so that the mechanism will work when displacement is translated from the actuation wires to the force members. The slots can also be filled in with a material such as glue after the tip of the actuation wire is placed into the force member wherein the glue acts as a secondary connection system.

The actuation wires 125 connect to the button 130 at locations near the top of the button, as shown in FIG. 15. The actuation wires can be inserted into openings at the top of the button where the user actuates the mechanism and the wire clamped at the end of the guide members to ensure that the wires do not shift and that equal displacement is transferred to both force members 120.

The aforementioned assemblies are just example and variations are within the scope of this disclosure.

Implantation Procedure

The device 105 is surgically implanted into a patient by inserting the patient's urethra into the urethral opening of the device. The implantation procedure can optionally vary based on whether the patient is male or female.

For female patients, the device 105 can be implanted from an abdominal approach on the superior surface of the urethra so that the gap 109 of the device 105 faces towards the vagina. The device is oriented such that thicker portions of the device are situated away from the vaginal wall to discourage erosion. The button and actuation assembly may be placed elsewhere in the body at a remote location from the device and from the urethra just under the skin, such as at the anterior pelvic area where there is enough back pressure to operate the button mechanism.

The actuation wires may be extended from the force members, through the rigid guide members of the skeleton, through the base of the skeleton, to the remote location of the actuation assembly. The guide members remain rigid within the region located inside the casing of the device. However, the guide members can transition to a softer material (such as an elastomer) in the region extending from the casing to the remote button. During surgery the surgeon thread the softer guide member and actuation wire under the skin to connect the cuff to the actuation assembly.

For a male patient, the surgeon makes a perineal incision along the sagittal plane and clears away tissues, membranes, and muscle to expose the bulbar urethra. The surgeon clears space lateral to the urethra on either side, but does not have to make a blind incision on the superior side of the urethra to separate the urethra from the tunica albuginea. The surgeon then measures the approximate diameter of the urethra to choose the appropriate device 105 to implant such that the opening in the device 105 is proper for the size of the urethra.

The device 105 can be provided in different sizes to accommodate different sized urethras. When the cuff changes in diameter, this may be accompanied by corresponding changes in the dimensions of the skeleton, actuation wires, force members, and actuation assembly. After dissecting around the urethra and measuring the diameter of the urethra, the surgeon chooses the appropriately sized device to implant. To implant, the surgeon carefully pull apart the two sides of the device to expand the gap 109 and slip the cuff onto the urethra through the gap 109 such that the urethra is positioned in the opening. Once the device is secured around the urethra, the surgeon may adjust the position and placement of the device along the urethra. The surgeon can test the device during surgery to ensure sufficient compression is achieved with the chosen size before closing the incision and ending the surgery.

The surgeon has the option of using the strap (FIGS. 5A and 5B and 6) that wraps completely circumferentially around the urethra. If the surgeon decides that more security is needed by use of the strap, the surgeon cuts completely around the urethra and through the tunica albuginea. The strap is then secured to one side of the cuff before being threaded behind the urethra and secured on the opposite side of the cuff.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. An artificial urinary sphincter for treating urinary incontinence, comprising:
    an annular body defining a urethral opening with a gap sized and shaped to receive a urethra upon the body being implanted into a patient, wherein the gap provides a passageway for the urethra to be inserted into the urethral opening;
    at least one force member movably attached to the body, the force member movable between a closed position such that the force member inhibits urine flow through the urethra when implanted, and an open position such that the force member does not inhibit fluid flow through the urethra when implanted;
    an actuation assembly coupled to the body and to the at least one force member, the actuation assembly including an actuator coupled to an actuation mechanism contained entirely within the body, wherein actuation of the actuation mechanism causes movement of the force member between the closed position and the open position.

2. An artificial urinary sphincter as in claim 1, wherein the body comprises an outer casing and an internal skeleton at least partially disposed inside the outer casing.

3. An artificial urinary sphincter as in claim 2, wherein the internal skeleton is more rigid than the outer casing.

4. An artificial urinary sphincter as in claim 2, wherein the outer casing is made of silicone.

5. An artificial urinary sphincter as in claim 1, wherein the body at least partially surrounds the urethra when implanted.

6. An artificial urinary sphincter as in claim 1, further comprising a retaining member on the body, wherein the retaining member interacts with adjacent tissue in a manner that fixes a position of the artificial urinary sphincter relative to tissue when implanted.

7. An artificial urinary sphincter as in claim 6, wherein the retaining member is a wing that extends outwardly from the body.

8. An artificial urinary sphincter as in claim 1, wherein the at least one force member comprises a pair of force members each having an abutment surface that faces toward the urethral opening.

9. An artificial urinary sphincter as in claim 8, wherein the pair of force members face toward one another.

10. An artificial urinary sphincter as in claim 1, wherein the at least one force members moves inward toward the urethral opening as it transitions from the open position to the closed position.

11. An artificial urinary sphincter as in claim 1, wherein the at least one force members moves away from the urethral opening as it transitions from the closed position to the open position.

12. An artificial urinary sphincter as in claim 1, wherein the force member exerts a force onto the urethra sufficient to completely block urine flow through the urethra when implanted and in the closed position.

13. An artificial urinary sphincter as in claim 8, wherein the at least one force member comprises an abutment surface that is at least one of a flat surface, a curved surface, a concave surface, and a convex surface.

14. An artificial urinary sphincter as in claim 8, wherein the pair of force members exert parallel force vectors toward the urethra.

15. An artificial urinary sphincter as in claim 8, wherein the pair of force members exert nonparallel force vectors toward the urethra.

16. An artificial urinary sphincter as in claim 1, wherein the actuator of the actuation assembly is a button.

17. An artificial urinary sphincter as in claim 16, wherein the button can be pressed to transition the at least one force member between the open position and the closed position.

18. An artificial urinary sphincter as in claim 1, wherein the entire actuation assembly is contained within the body.

19. An artificial urinary sphincter as in claim 1, wherein at least a portion of the actuation assembly is outside the body.

20. An artificial urinary sphincter as in claim 1, wherein the actuator is remotely located relative to the body.

21. An artificial urinary sphincter as in claim 1, further comprising an actuator wire that mechanically attaches the actuator to the at least one force member.

22. An artificial urinary sphincter as in claim 21, wherein the actuator wire is part of the actuation assembly.

23. An artificial urinary sphincter as in claim 21, wherein the body comprises an outer casing and an internal skeleton at least partially disposed inside the outer casing, and wherein the actuator wire extends through the internal skeleton.

24. An artificial urinary sphincter as in claim 23, wherein the internal skeleton includes a tubular guide member having an internal lumen through which the actuator wire extends.

* * * * *